US008940118B2

(12) United States Patent
Schneider

(10) Patent No.: US 8,940,118 B2
(45) Date of Patent: Jan. 27, 2015

(54) BELT ATTACHMENT PROCESS FOR AN ABSORBENT ARTICLE

(75) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 56 days.

(21) Appl. No.: 13/315,357

(22) Filed: Dec. 9, 2011

(65) Prior Publication Data

US 2012/0152447 A1 Jun. 21, 2012

Related U.S. Application Data

(60) Provisional application No. 61/424,923, filed on Dec. 20, 2010.

(51) Int. Cl.
| | | |
|---|---|---|
| *B32B 37/00* | (2006.01) | |
| *B23P 17/04* | (2006.01) | |
| *B31B 1/26* | (2006.01) | |
| *B32B 38/00* | (2006.01) | |
| *A61F 13/15* | (2006.01) | |
| *A61F 13/49* | (2006.01) | |

(52) U.S. Cl.
CPC ..... *A61F 13/15747* (2013.01); *A61F 13/15764* (2013.01); *A61F 13/49061* (2013.01)
USPC ................ 156/227; 156/60; 29/464; 493/405

(58) Field of Classification Search
CPC .................... A61F 13/15747; A61F 13/49061; A61F 13/15764
USPC .............................. 156/227, 60; 604/385.101
See application file for complete search history.

(56) References Cited

U.S. PATENT DOCUMENTS

| | | | | | |
|---|---|---|---|---|---|
| 4,964,860 | A | * | 10/1990 | Gipson et al. | 604/391 |
| 5,151,092 | A | * | 9/1992 | Buell et al. | 604/385.3 |
| 5,702,551 | A | * | 12/1997 | Huber et al. | 156/73.1 |
| 5,779,831 | A | | 7/1998 | Schmitz | |
| 6,248,195 | B1 | | 6/2001 | Schmitz | |
| 6,336,922 | B1 | * | 1/2002 | VanGompel et al. | 604/385.3 |
| 6,450,321 | B1 | | 9/2002 | Blumenthal et al. | |
| 6,632,213 | B1 | * | 10/2003 | Lehman et al. | 604/385.25 |
| 6,830,566 | B2 | | 12/2004 | Kuen et al. | |

(Continued)

FOREIGN PATENT DOCUMENTS

WO WO 2008/143951 A1 11/2008

OTHER PUBLICATIONS

PCT International Search Report dated Mar. 26, 2012, 10 pages.

*Primary Examiner* — Michael Orlando
*Assistant Examiner* — Marta Dulko
(74) *Attorney, Agent, or Firm* — Sarah M. DeCristofaro; Abbey A. Lopez

(57) ABSTRACT

A method and device for assembling diapers of intentionally varied size. The method may comprise providing a series of waist belts having a fixed longitudinal length, and a series of chassis having a fixed longitudinal length. The waist belts may be aligned with the chassis with varying degrees of overlap, such that diapers having different lengths are manufactured by varying only the relative placement of the waist belts and chassis. The method may be used to vary diapers within a production run (e.g., to produce packs of diapers in a range of sizes) or between production runs (e.g., to produce different size diapers on the same line with reduced equipment changes or adjustments). A diaper produced according to the method is also described.

19 Claims, 11 Drawing Sheets

(56) References Cited

U.S. PATENT DOCUMENTS

| | | |
|---|---|---|
| 7,146,893 B2 | 12/2006 | Aichele |
| 7,252,730 B2 * | 8/2007 | Hoffman et al. ............... 156/164 |
| 7,322,925 B2 | 1/2008 | Couillard et al. |
| 7,335,190 B2 * | 2/2008 | Underhill et al. ........ 604/385.01 |
| 7,368,027 B2 | 5/2008 | Schneider et al. |
| 7,399,266 B2 | 7/2008 | Aiolfi et al. |
| 7,591,810 B2 * | 9/2009 | Morman et al. .......... 604/385.24 |
| 7,753,099 B2 | 7/2010 | Schneider et al. |
| 2004/0122412 A1 * | 6/2004 | Morman et al. ....... 604/385.101 |
| 2005/0020991 A1 | 1/2005 | Van Gompel et al. |
| 2005/0148965 A1 | 7/2005 | Richlen et al. |
| 2005/0288646 A1 * | 12/2005 | LaVon .................... 604/385.28 |
| 2006/0116655 A1 | 6/2006 | Van Gompel et al. |
| 2008/0196564 A1 * | 8/2008 | McCabe .......................... 83/23 |
| 2009/0312732 A1 * | 12/2009 | LaVon et al. .................. 604/378 |

\* cited by examiner

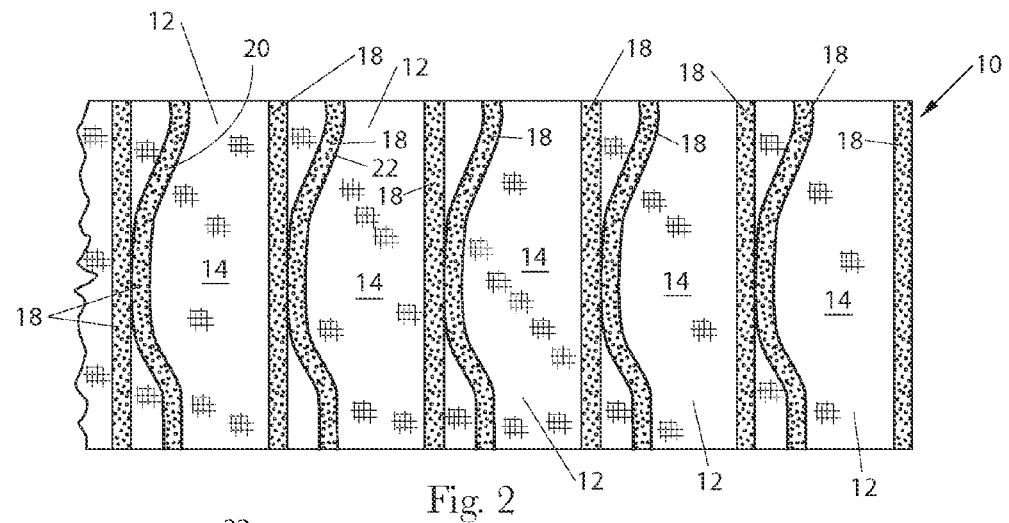
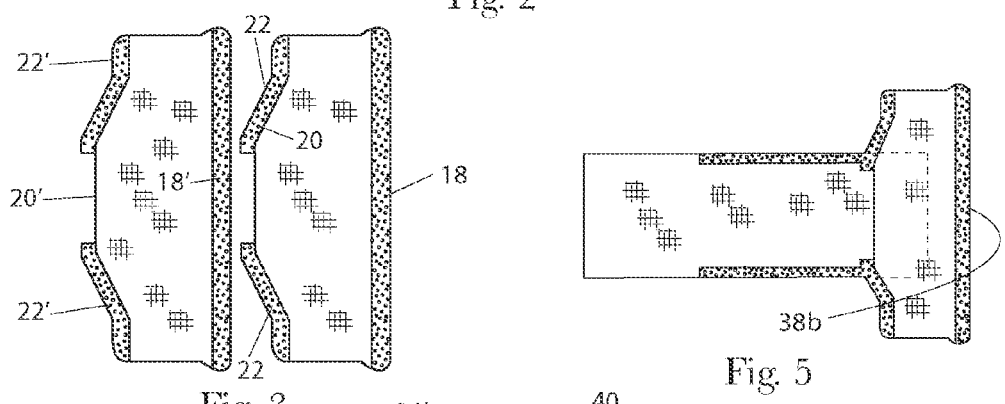
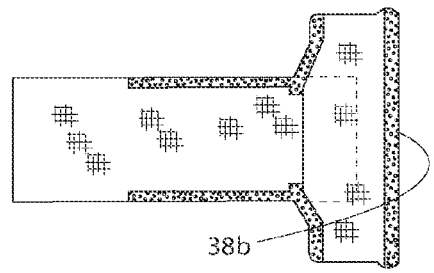
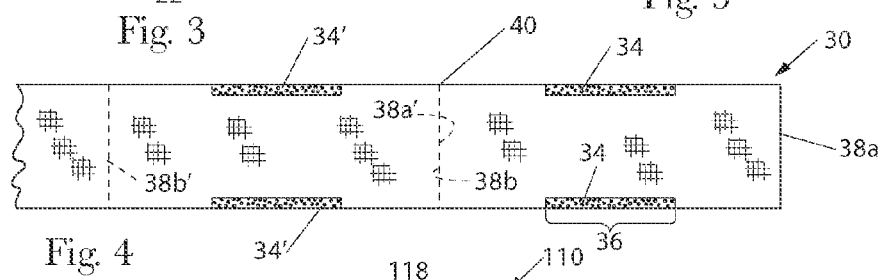
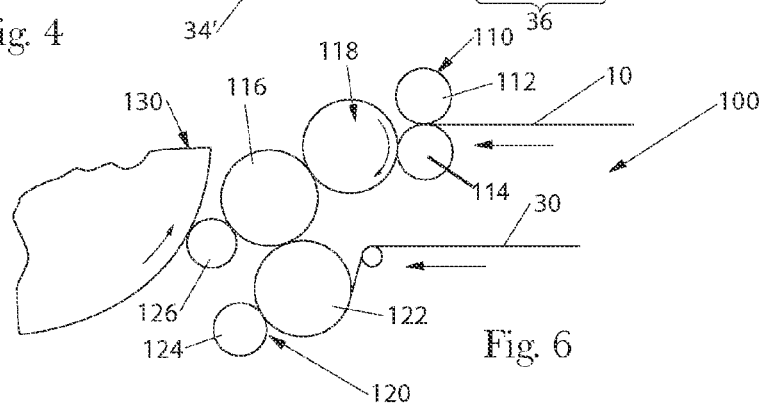

BELT ATTACHMENT PROCESS FOR AN ABSORBENT ARTICLE

CROSS REFERENCE TO RELATED APPLICATION

This application claims the benefit of U.S. Provisional Application No. 61/424,923, filed on Dec. 20, 2010, which is incorporated herein by reference.

FIELD OF THE INVENTION

The invention generally relates to methods of attaching one web of material to another web of material. In particular, the invention relates to a method of attaching a belt or waist portion of a diaper to a main diaper chassis.

BACKGROUND OF THE INVENTION

Infants and other incontinent individuals wear disposable absorbent articles such as diapers to absorb and retain urine and other body exudates. Absorbent articles may function both to contain the discharged materials and to isolate these materials from the body of the wearer and from the wearer's garments and bed clothing. Diaper users of all ages present a variety of body shapes and sizes. Thus, diapers are generally provided in a range of sizes to accommodate different body types and sizes. A particular diaper wearer, such as an infant or young child, may also grow rapidly. Diapers are sometimes sold in "bulk packs" containing large quantities of diapers, which may contain 200 diapers or more in a single sales unit. However, an infant may need a larger diaper size before an entire bulk pack is used. Thus, purchasing diapers presents a conundrum for caregivers, who must wager on whether they should spend more (per diaper) for a smaller pack of diapers, so that an infant is unlikely to outgrow the diaper size before the diapers are used, or whether they should spend less (per diaper) for a bulk pack of diapers, some portion of which may be discarded if the diapers are outgrown by the infant before all the diapers are used. This problem may also arise with incontinent adults, such as recovering invalids who are regaining weight lost during illness or injury.

Diapers can be configured to fit on a wearer's body in various ways. For example, some diapers may be configured as pull-on, pant-type diapers or training pants. Diapers, including training pants, may be used with infants prior to and/or during toilet training. Training pants may be configured with a "closed" chassis configuration, in which the chassis is adapted to be pulled on over the legs and lower torso of the wearer without any additional fastening steps. Other diapers may be configured as a "taped diaper," in an "open" chassis configuration, in which the chassis is adapted to be applied to the wearer by wrapping the diaper around the user and fastening the diaper to itself, usually at or near the waist of the wearer.

Closed chassis diapers may be manufactured with a front ear being seamed to a back ear to form the closed chassis. In some configurations, closed chassis diapers may also have manually tearable side seams. The side seams may be configured as butt-type seams or overlapping side seams.

During the manufacturing process, a closed chassis diaper may be manufactured from a blank cut to a particular configuration and size. Manufacturing processes may involve some type of sealing step to create side seams in the diapers. For example, after being fully assembled, the blank may be folded along a central transverse area and the sides of the front and rear panels are seamed together to form a closed chassis diaper. In other processes, the side seams may be formed by folding the chassis in a crotch portion so that longitudinal side regions of the front portion and rear portion are superposed to form seaming areas, which are then treated with ultrasonic energy to sever the material in the seaming area in a first area while simultaneously bonding the material of the seaming area in a marginal area adjacent the first area to form a flangeless seam.

In some manufacturing configurations, the seaming and folding operations may be performed automatically on a processing wheel having a plurality of folding stations and associated seaming mechanisms. Various types of such processing wheels have been described in U.S. Patent Publication No. 2008/0083489 and U.S. Pat. Nos. 5,779,831 and 7,322,925, each of which is hereby incorporated by reference herein.

The processing wheels provide the ability to produce training pants at a high rate of speed. However, reconfiguring various components of the processing wheel to change manufacturing operations for different sizes of absorbent articles can be onerous. For example, some components of the processing wheel may require realignment, which can be time consuming and expensive. For instance, different size folding stations may be needed to accommodate a different sized diaper. Such different sized folding stations may need to be realigned with the seaming stations. In addition, different sized folding stations may also require changes in the physical locations of operating stations, such as the discharge station, located adjacent the processing wheel.

Prior methods of manufacturing diapers suffered from problems of difficulty of control of the web material and the diaper subcomponents. Because of the control difficulty, prior methods were limited in overall production speed and produced a lower quality end product. Furthermore, every different size of diaper required a different machine that was sized to seam the individual size of diaper. As a result, diaper production required separate production lines for each size of diaper, which resulted in large capital outlays and more expensive maintenance.

SUMMARY OF THE INVENTION

A method of attaching a waist belt to a diaper chassis may include forming a waist belt, forming a diaper chassis and attaching the waist belt to the diaper chassis. The waist belt may be formed in a machine direction or in a cross direction. After attaching the waist belt to the diaper chassis, the diaper chassis may be folded about one or more axes, free ends of the waist belt may be folded relative to the diaper chassis, and the free ends of the waist belt may be seamed to the diaper chassis, forming a pant-type diaper. The steps of attaching the waist belt to the diaper chassis, folding the diaper chassis, folding the free ends of the waist belt, and seaming the free ends of the waist belt may be performed on machines that are close-coupled.

A machine for attaching a waist belt to a diaper chassis may include a waist cutting and spacing device that cuts and spaces discrete waist belts from a web of waist belt material. The cutting and spacing device may deliver the discrete waist belts to an integral servo pitch placer. The machine may also include a diaper chassis cutting device that cuts discrete diaper chassis from a web of diaper chassis material. The machine may deliver the discrete diaper chassis to a space and bond drum, wherein the discrete waist belts are attached to respective discrete diaper chassis. The combined waist belt and diaper chassis may be side seamed in a final folding and seaming machine to form a pant-type diaper.

An apparatus and method for assembling diapers of varying sizes. The method may comprise providing a series of waist belts and a series of chassis. Each waist belt may have a uniform longitudinal length L1, and each chassis may have a uniform longitudinal length L2. A waist belt from the series of waist belts may be aligned with a chassis from the series of chassis. The waist belt may extend longitudinally beyond the chassis. The length of the chassis plus the length of the waist belt extending beyond the chassis may equal a desired chassis length. The waist belt may be attached to the chassis. The apparatus may comprise a cutting means for separating the waist belts from one another and/or the chassis from one another, and a spacing means for longitudinally positioning the waist belts and/or the chassis. The apparatus may comprise aligning means for positioning the waist belts in a desired position relative to the chassis, in the machine- or cross-directions. The apparatus may further comprise joining means for joining the waist belt and the chassis.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 2 is a top plan view of a first web of material that will become a belt or waist portion of a diaper.

FIG. 3 is a top plan view of the web of material of FIG. 2 cut in the shape of a waist belt.

FIG. 4 is a top plan view of a second web of material that will become a main chassis of a diaper.

FIG. 5 is a top plan view of the waist belt attached to the main chassis.

FIG. 6 is a schematic view of a machine that attaches a belt or waist portion of a diaper to a main diaper chassis.

DETAILED DESCRIPTION OF THE INVENTION

Figure 1A:
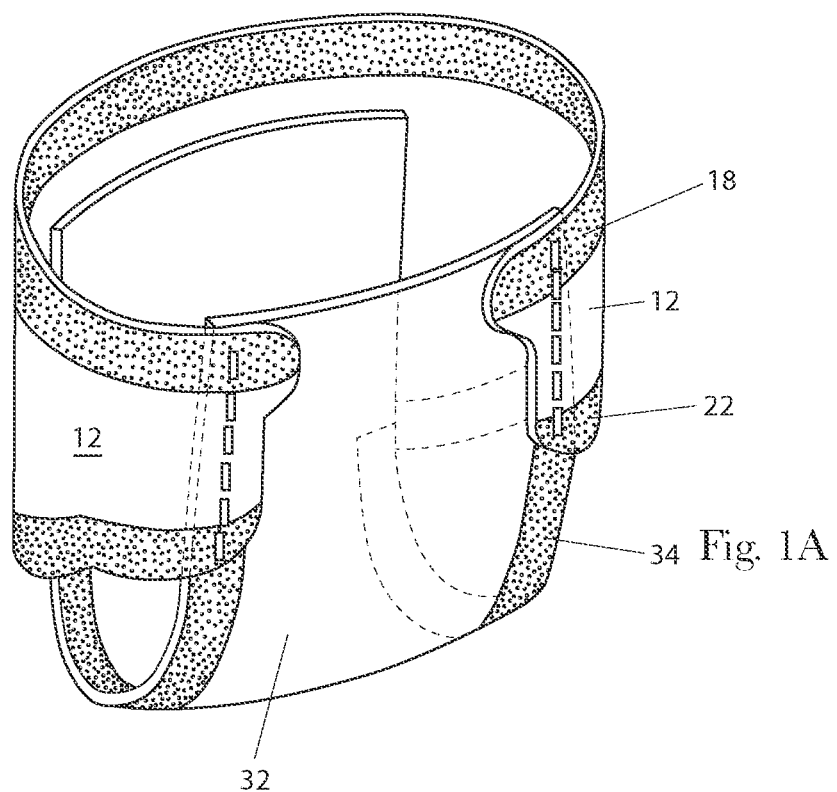
FIG. 1A is a front perspective view of a diaper constructed in accordance with the teachings of the disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

The following term explanations may be useful in understanding the present disclosure:

"Absorbent article" is used herein to refer to consumer products whose primary function is to absorb and retain bodily soils and wastes, such as urine, feces, or menses. "Diaper" is used herein to refer to an absorbent article generally worn by infants and incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "close coupled" means nearly touching (i.e., a separation of about 20 mm, or 10 mm, or less). For example, machines that are close coupled may be separated from one another by about 10 mm or less and separate manufacturing stations on a single machine that are close coupled may be separated from one another by about 10 mm or less.

The term "disposed" is used herein to mean that an element (s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" or "web" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers of fibrous materials, films and foils, such as nonwoven materials, elastic films, or plastic films, that may be used alone or laminated to one or more layers, films and/or foils. The different layers of a laminate may be of the same or different materials, and the materials may be different in their composition or configuration. For example, a laminate may comprise two layers of a nonwoven having the same composition (e.g., polypropylene) and basis weight, or two layers of nonwovens having different compositions (e.g., polypropylene and a polypropylene/viscose blend) in the same or different basis weights, or one layer of a nonwoven and one layer of a film, and so on.

The term "nonwoven" refers herein to a material made from continuous (long) filaments (fibers) and/or discontinuous (short) filaments (which may also be referred to as fibers) by processes such as spunbonding, meltblowing, airlaying, wetlaying, coforming, and the like. Nonwovens do not have a woven or knitted filament pattern.

The term "machine direction" (MD) is used herein to refer to the direction of material flow through a process.

The term "cross direction" (CD) is used herein to refer to a direction that is generally perpendicular to the machine direction, including directions within ±40° from the direction perpendicular to the machine direction.

The terms "activating", "activation" or "mechanical activation" refer to the process of making a substrate, or an elastomeric laminate more extensible than it was prior to the process.

"Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

"Film based elasticity" is a process of forming a laminate by attaching one or more non-woven layers to an elastic layer while the elastic layer is in a relaxed or un-stretched state. After the laminate is formed, the laminate is placed under tension to the point where the non-woven layers are deformed in the direction of tension by plastic fiber elongation or by breaking fibers in the non-woven (which may be described as activation). After the tension is released, the elastic layer may recoil to its original length and, in doing so, the non-woven layers are gathered, forming a corrugated structure.

Aspects of the present disclosure relate to methods and apparatuses for manufacturing absorbent articles (e.g., diapers) having a waist belt attached to a diaper chassis, and more particularly, apparatuses and methods of forming the waist belt in a machine direction or a cross direction by laminating two or more webs of material together. After formation of the waist belt, the waist belt is attached to the diaper chassis. Depending on which orientation was used when forming the waist belt (i.e., machine direction or cross direction), the waist belt may or may not need to be rotated into proper alignment with the diaper chassis. Particular embodiments of apparatuses and methods of manufacture disclosed herein include one or more assembly lines for forming the waist belt and diaper chassis, a joining apparatus for attaching the waist belt to the diaper chassis, and a processing wheel having a plurality of processing stations which orbit around a rotation axis for forming side seams on the diaper chassis and waist belt. As the processing stations move along an orbit path, the processing stations may perform various operations, such as folding the blanks and superimposing sealing areas on the folded blanks. The processing stations may also move the sealing areas into a position to a desired alignment with a sealing station where the sealing areas are connected. Once the processing stations have performed the required operations, the absorbent articles may be moved from the processing wheel to another apparatus used in the manufacturing operation.

In some aspects, the present disclosure relates to a method and apparatus for producing diapers of varying sizes. The method may comprise aligning waist belts of a given length with chassis of a given length in different relative positions, such that the overall length of the diaper formed by the method is different even though the starting components are of fixed dimensions. The method may allow for the production of intentionally different diaper sizes with limited, or even no, equipment changes. The method may also allow for the production of incrementally sized diapers, with small or even very small differences between diapers of different sizes, in contrast to the conventional practice of producing diapers of starkly different sizes. The apparatus may include means for aligning the waist belts and the chassis in different relative positions.

Figure 1B:
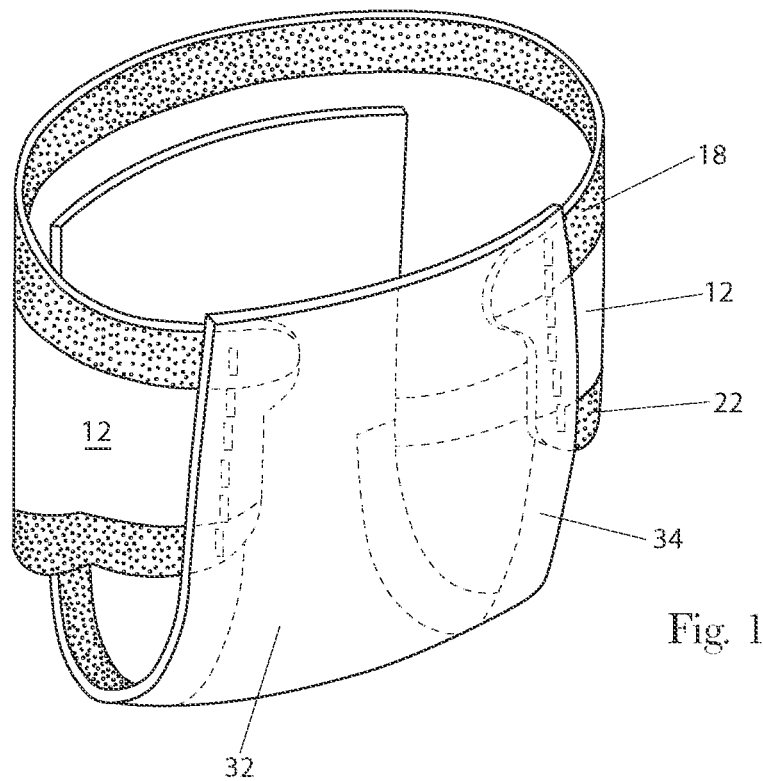
FIG. 1B is a front perspective view of an alternate embodiment of a diaper constructed in accordance with the teachings of the disclosure.

FIGS. 1a and 1b illustrate two embodiments of a diaper constructed in accordance with the teachings of the disclosure. The diaper generally includes a diaper chassis 32 and a waist belt 12 attached to one another to form a pant-type diaper. The diaper chassis 32 may include strips of elastic 34 that form a portion of a leg opening for the diaper. Likewise, the waist belt 12 may include elastic in an upper waist region 18 and in a leg opening region 22. The main difference between the embodiment of FIG. 1a and the embodiment of FIG. 1b is that the waist belt 12 of the embodiment of FIG. 1a is seamed outside of the diaper chassis 32, while the waist belt 12 of the embodiment of FIG. 1b is seamed inside the diaper chassis 32.

Referring now to FIGS. 2 and 3, a web of waist belt material 10 is illustrated that will be cut to form a plurality of waist belts 12. Initially, webs of non-woven material 14 are bonded to webs of elastic material 16 forming the laminate web of waist belt material 10. After the webs are bonded, the waist belt material 10 is subject to tension in the cross direction until the non-woven material deforms, thereby giving the waist belt material 10 film based elasticity, as described above. In some embodiments, the waist belt material may be formed in a ring roll process or another similar process. In yet other embodiments, the waist belt material may be formed with live stretch. After the waist belt material 10 acquires its elasticity, the waist belt material 10 is cut to form the discrete waist belts 12 illustrated in FIG. 3.

The discrete waist belts 12 include the upper waist region 18, a lower waist region 20, and two leg opening regions 22. In forming the discrete waist belts 12 from the web of waist belt material 10, portions of the web of waist belt material are trimmed in the areas of the leg opening regions 22 and between the lower waist region 20 of one discrete waist belt 12 and the upper waist region 18 of another waist belt 12'. Elastic material may also be trimmed from the center of the lower waist region 20 in the region where the lower waist region 20 will overlap with the diaper chassis 32.

In a similar operation (FIG. 4), discrete diaper chassis 32 may be formed from a web of diaper chassis material 30.

Strips of elastic 34 may be bonded to the web of diaper chassis material 30 in a crotch area 36 of the discrete diaper chassis 32. In contrast to the waist belts 12 above, the discrete diaper chassis 32 may utilize live stretch when bonding the elastic 34 to the diaper chassis material 30 to produce a desired level of elasticity in the regions of the strips of elastic 34. Alternatively, the discrete diaper chassis 32 may be formed with film based elasticity. The discrete diaper chassis 32 may also include front and back waist regions 38a and 38b, respectively. After separation, the discrete diaper chassis 32 may be spaced from one another for joining to the waist belts 12.

As illustrated in FIG. 5, one discrete waist belt 12 may be attached to one discrete diaper chassis 32 by overlaying the discrete waist belt 12 on the back waist region 38b (or alternatively by overlaying the back waist region 38b on the waist belt 12) such that the elastic 16 on the lower waist region 18 of the waist belt 12 is proximate the elastic 34 in the leg region 36 of the discrete diaper chassis 32. The elastic 16 on the lower waist region 18 of the waist belt 12 will be connected to the elastic 34 of the discrete diaper chassis 32 to form a continuous leg hoop. In other embodiments, the discrete waist belt 12 may be joined to the discrete diaper chassis 32 in the vicinity of the front waist region 38a of the discrete diaper chassis 32. The discrete waist belt 12 may be joined to the discrete diaper chassis 32 by virtually any method, such as, adhesives, cohesives, hook and loop fasteners, thermo bonding, pressure bonding, or ultrasonic bonding.

A machine 100 that performs the method of joining the waist belts 12 to diaper chassis 32 is illustrated schematically in FIG. 6. The waist belt web 10 and the diaper chassis web 30 enter the machine as continuous webs of material. Discrete waist belts 12 are cut from the waist belt web 10 by a cutting and spacing station, including a cutting device 110 followed by a spacing device 118. The cutting device 110 may include a belt anvil 112 and a belt knife 114. The spacing device 118 may include a servo spacing device that is servo cammed or actuated in some other manner, such as by a mechanical cam. Of course, other methods and devices for spacing and cutting the waist belts 12 may also be used. For example, the waist belt web 10 may be provided with pre-formed perforations defining the discrete waist belts and the discrete waist belts 12 may be separated by tearing along the perforations. As the waist belt web 10 moves through the cutting device 110, the speed of the waist belt material increases in the machine direction after the discrete waist belts 12 are cut so that the discrete waist belts 12 are spaced apart from one another. In other words, the speed of the waist belt web (or material) 10 in the machine direction is slower before entering the cutting device 110 than after exiting the cutting device 110. After being cut and/or separated by the cutting device 110, the discrete waist belts 12 are applied to a space and bond drum 116 by servo driven or cammed patch spacing device 118. One example of a servo driven or cammed patch spacing device 118 is disclosed in U.S. Pat. No. 6,450,321, which is incorporated herein by reference.

While the waist belts 12 are being cut and/or spaced, the diaper chassis 32 are formed concurrently in a parallel operation. The web of diaper chassis material 30 enters the machine 100 and is cut by a cutting device 120. The cutting device may include a final knife 122 and a final knife anvil 124. In other embodiments, the diaper chassis material 30 may be supplied with pre-formed perforations defining discrete diaper chassis 32. As the web of diaper chassis material 30 moves through the cutting device 120, the speed of the diaper chassis material increases in the machine direction after the discrete diaper chassis 32 are cut so that the discrete diaper chassis 32 are spaced apart from one another. In other words, the speed of the diaper chassis material in the machine direction is slower before entering the cutting device 120 than after exiting the cutting device 120. Although the spacing process of the diaper chassis 32 is similar to the spacing process of the waist belts 12, the relative speeds may differ such that the space between discrete diaper chassis 32 may be greater than or less than the spacing between discrete waist belts 12. After being cut and/or separated, the diaper chassis 32 are applied to the space and bond drum 116. After the diaper chassis 32 is applied to the space and bond drum 116, the space and bond drum rotates (clockwise in FIG. 6) towards the servo driven or cammed patch spacing device 118. As the diaper chassis 32 passes by the servo driven or cammed patch spacing device 118, the servo driven or cammed patch spacing device 118 applies a waist belt 12 to the diaper chassis 32 in the orientation illustrated in FIG. 5. After the waist belt 12 and the diaper chassis 32 are joined on the space and bond drum 116, the waist belt 12 may be seamed or joined to the diaper chassis 32. The combined waist belt 12 and diaper chassis 32 are transferred to a final folding and seaming device 130 by a transfer drum 126. Examples of a final folding and seaming 130 device are illustrated and described in U.S. Pat. No. 5,779,831 and U.S. Patent Publication No. 2008/0083489, each of which is hereby incorporated by reference herein. In other embodiments, separate final folding and seaming devices may be used. Examples of such separate final folding devices may be found in U.S. Pat. No. 7,399,266 (twisting conveyor) and U.S. Pat. No. 7,368,027 (folding drum), which are hereby incorporated by reference herein. In yet other embodiments, the combined waist belt 12 and diaper chassis may be transferred directly to the final folding and seaming device 130 from the space and bond drum 116. The final folding and seaming device 130 folds the diaper chassis 32 about one or more axes, folds free ends of the waist belt 12 relative to the diaper chassis 32, and attaches the free ends of the waist belt 12 to the front waist region 38a of the diaper chassis 32, thereby forming a complete pant-style diaper. A more detailed description of the final folding and seaming device 130 is provided below with reference to FIGS. 13-16.

One advantage to the embodiments illustrated in FIGS. 2-6 is that the waist belts 12 are formed with cross directional extensibility. Thus, the discrete waist belts 12 do not need to be rotated prior to positioning the waist belt 12 over the front waist region 38a of the diaper chassis 32. In other words, the discrete waist belts 12 may pass from the cutting device 110 directly to the servo driven or cammed patch spacing device 118 in this embodiment.

Figure 7:
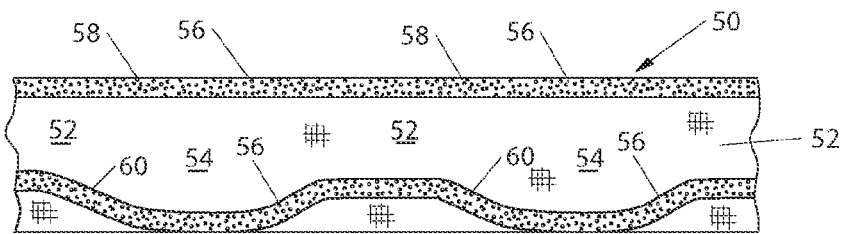
FIG. 7 is a top plan view of an alternative embodiment of a first web of material that will become a belt or waist portion of a diaper.
Figure 9:
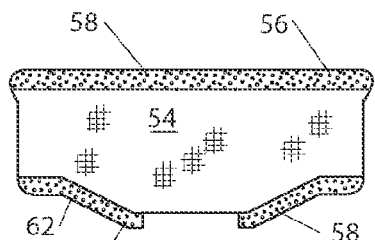
FIG. 9 is a top plan view of the first web of material of FIG. 8 including a notched out portion of elastic.
Figure 8:
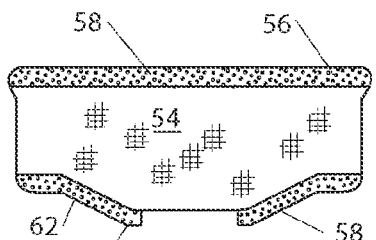
FIG. 8 is a top plan view of the alternative first web of material of FIG. 7 cut in the shape of a waist belt.

Referring now to FIGS. 7-9, an alternate embodiment of a web of waist belt material 50 is illustrated that will be cut to form a plurality of waist belts 52. Initially, webs of nonwoven material 54 are bonded to webs of elastic material 56 forming the laminate web of waist belt material 50. The waist belts 52 in the embodiment of FIGS. 7-9 may be formed in the machine direction and thus, a live stretch technique may be used to impart elasticity to the waist belts 52. In other embodiments, film based stretch may be used to form the waist belts 52. After the waist belt material 50 is formed (such as by a process involving live stretch, wherein elastics are tensioned and bonded to a relaxed nonwoven substrate, or other carrier material, using glue or other suitable adhesive, and then releasing the tension, upon which the elastics contract and the nonwoven substrate or other carrier material develops corrugations), the waist belt material 50 may be cut to form the discrete waist belts 52 illustrated in FIG. 8. In other embodiments, the waist belt material 50 may be supplied with pre-formed perforations.

The discrete waist belts 52 include an upper waist region 58, a lower waist region 60, and two leg opening regions 62. In forming the discrete waist belts 52 from the web of waist belt material 50, portions of the web of waist belt material are trimmed in the areas of the leg opening regions 52 and the discrete waist belts 52 are separated from one another along a width of the web of waist belt material 50.

Figure 10:
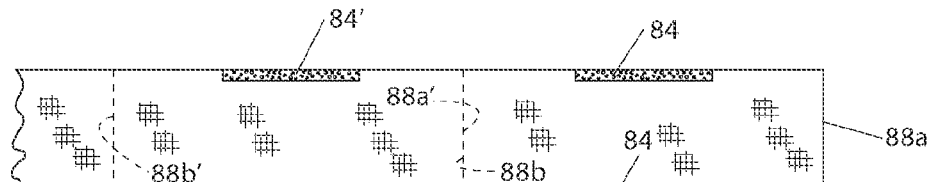
FIG. 10 is a top plan view of an alternative embodiment of a second web of material that will become a main chassis of a diaper.

In a similar operation (FIG. 10), a plurality of discrete diaper chassis 82 may be formed from a web of diaper chassis material 80. Strips of elastic 84 may be bonded to the web of diaper chassis material 80 in a crotch area 86 of the discrete diaper chassis 82. Like the waist belts 52 above, the plurality of discrete diaper chassis 82 in the embodiment of FIG. 10 may be formed in the machine direction and thus, live stretch may be used when bonding the elastic 84 to the diaper chassis material 80 to produce a desired level of elasticity in the regions of the strips of elastic 84. The elastic 84 may be positioned at the laterally outward-most edges of the chassis 82, such that in use elastic 84 forms a leg band around the leg of a user (e.g., at least a portion of the leg opening of the diaper is elasticated). In alternative embodiments, the discrete diaper chassis 82 may be formed with film based elasticity. The discrete diaper chassis 82 may also include front and back waist regions 88a and 88b, respectively. After separation, the discrete diaper chassis 82 are spaced for joining to the waist belts 52.

Figure 11:
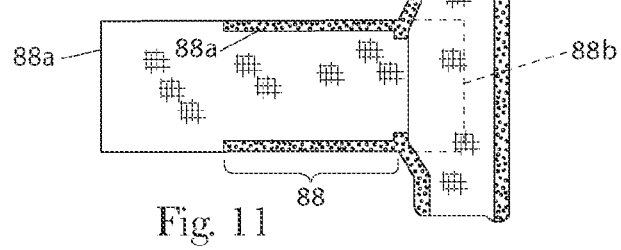
FIG. 11 is a top plan view of the alternative embodiment of the waist belt attached to the alternative embodiment of the main chassis.

As illustrated in FIG. 11, one discrete waist belt 52 is attached to one discrete diaper chassis 82 by overlaying the discrete waist belt 52 on the back waist region 88b such that the elastic 56 on the lower waist region 58 of the waist belt 52 is proximate the elastic 84 in the leg region 86 of the discrete diaper chassis 82. The elastic 56 on the lower waist region 58 of the waist belt 52 will be connected to the elastic 84 of the discrete diaper chassis 82 to form a continuous leg loop. The discrete waist belt 52 may be joined to the discrete diaper chassis 82 by virtually any method, such as, adhesives, cohesives, hook and loop fasteners, thermo bonding, pressure bonding, ultrasonic bonding, etc.

Figure 12:
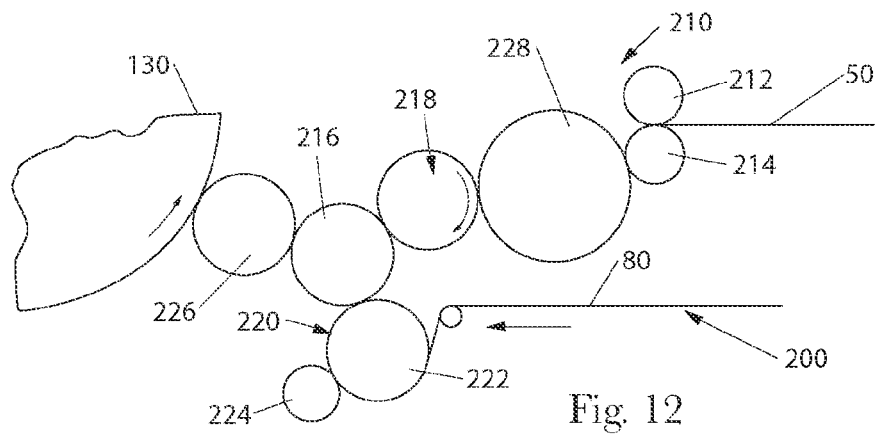
FIG. 12 is a schematic view of a second embodiment of a machine that attaches a belt or waist portion of a diaper to a main diaper chassis.

A machine 200 that performs the method of joining the waist belts 52 to diaper chassis 82 is illustrated schematically in FIG. 12. The waist belt web 50 and the diaper chassis web 80 enter the machine as continuous webs of material. Discrete waist belts 52 are cut from the waist belt web 50 by a cutting and spacing station, including a cutting device 210 followed by a spacing device 218. The cutting device 210 may include a belt anvil 212 and a belt knife 214. The spacing device 118 may include a servo spacing device that is servo cammed or actuated in some other manner, such as by a mechanical cam. Of course, other methods and devices for spacing and cutting the waist belts 52 may also be used, such as providing the web of waist belt material 50 with pre-formed perforations defining the discrete waist belts 52. After being cut by the cutting device 210, the discrete waist belts 52 are rotated approximately 90 degrees by a turning drum 228, because the discrete waist belts 52 were formed in the machine direction. The turning drum delivers the discrete waist belts 52 to the spacing device 218, which, in turn, delivers the discrete waist belts 52 to a space and bond drum 216.

While the waist belts 52 are being cut and spaced, the diaper chassis 82 are formed concurrently in a parallel operation. The web of diaper chassis material 80 enters the machine 200 and is cut by a cutting device 220. The cutting device may include a final knife 222 and a final knife anvil 224. Of course, the web of diaper chassis material 80 may be provided with pre-formed perforations defining discrete diaper chassis 82. After being cut and/or separated, the diaper chassis 82 are applied to the space and bond drum 216. After the diaper chassis 82 is applied to the space and bond drum 216, the space and bond drum rotates (clockwise in FIG. 12) towards the spacing device 218. As the diaper chassis 82 passes by the spacing device 218, the spacing device 218 applies a waist belt 52 to the diaper chassis 82 in the orientation illustrated in FIG. 11. After the waist belt 52 and the diaper chassis 82 are joined on the space and bond drum 216, the waist belt 52 may be seamed or joined to the diaper chassis 82. The combined waist belt 52 and diaper chassis 82 are transferred to a final folding and seaming device 130 by a transfer drum 226. In other embodiments, the combined waist belt 52 and diaper chassis 82 may be transferred directly to the final folding and seaming device 130 from the space and bond drum 216. The final folding and seaming device 130 folds the diaper chassis 82 about one or more axes, folds free ends of the waist belt 52 relative to the diaper chassis 82, and seams the free ends of the waist belt 52 to the front waist region 88a of the diaper chassis 82, thereby forming a complete pant-style diaper. A more detailed description of the final folding and seaming device 130 is provided below with reference to FIGS. 13-16.

One advantage to the embodiment illustrated in FIGS. 7-12 is that the waist belts 52 are formed in the machine-direction. When formed in the machine-direction, the live stretch technique is easier to employ due to the general alignment of the webs of elastic.

Figure 17A:
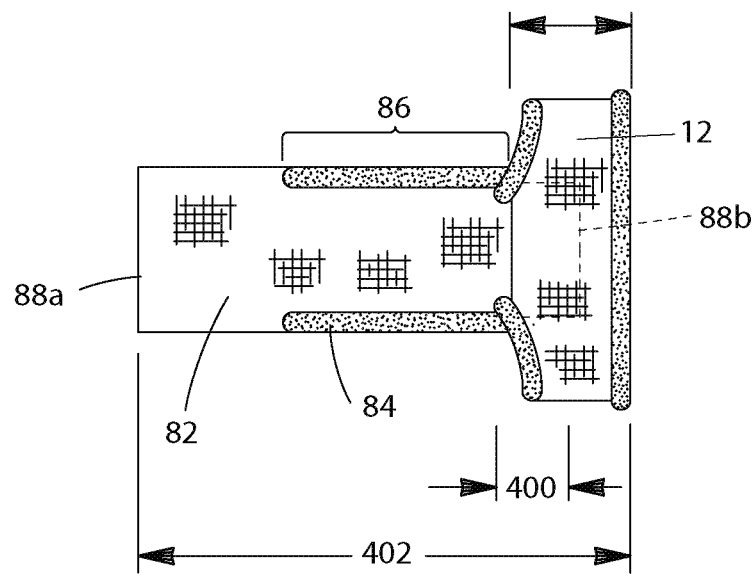
FIG. 17A is a schematic view of a waist belt aligned with a chassis in a first position.
Figure 17B:
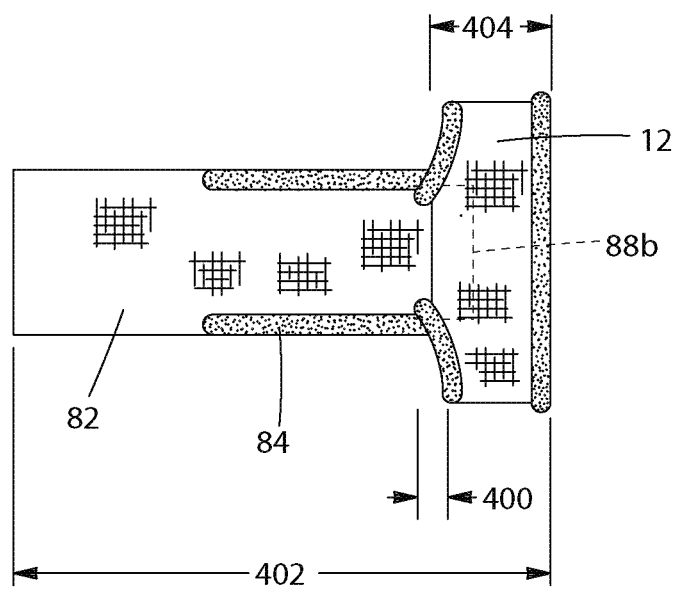
FIG. 17B is a schematic view of a waist belt aligned with a chassis in a second position.

The space and bond drum 216 and/or spacing device 218 may be configured to place the waist belt 52 in different positions relative to the diaper chassis 82. For example, FIG. 17A shows a diaper having chassis 82 and waist belt 12. The waist belt 12 has a length 404, which is placed overlapping a portion of back waist region 88b of chassis 82. The extent of the overlap is noted as length 400. The total length of the diaper having this overlap is 402. In contrast, FIG. 17B shows a diaper having a chassis 82 and waist belt 12 having the same lengths as the chassis 82 and waist belt 12 of FIG. 17A, respectively. However, the overlap length 400 is shorter in FIG. 17B, resulting in a longer overall diaper length 402. Thus, the relative placement of the chassis 82 and waist belt 12 can be used to alter the size of the diaper without changing the size of the incoming parts. For some range of sizes, the relative placement can be modified by changing the speed or relative speeds of the space and bond drum 216 and/or spacing device 218, such that different size diapers can be produced with no or minimal equipment or set-up changes. For example, it would not be necessary to change the dies or cutting rolls used to cut waist belt 12 or chassis 82 to shape and size. If the spacing apparatus are electronically controlled, it may even be possible to produce diapers of varying sizes in sequence. Thus, a package of diapers may include a series of sequentially larger diapers with modest differences in size between the diapers, so that even with a single package, the diapers "grow" with a baby or young child. This may be of particular, but not exclusive, interest for bulk packs, which may be consumed over a period of weeks or even months, and, thus, may be used over a time period in which an infant or young child may grow noticeably.

Figure 17C:
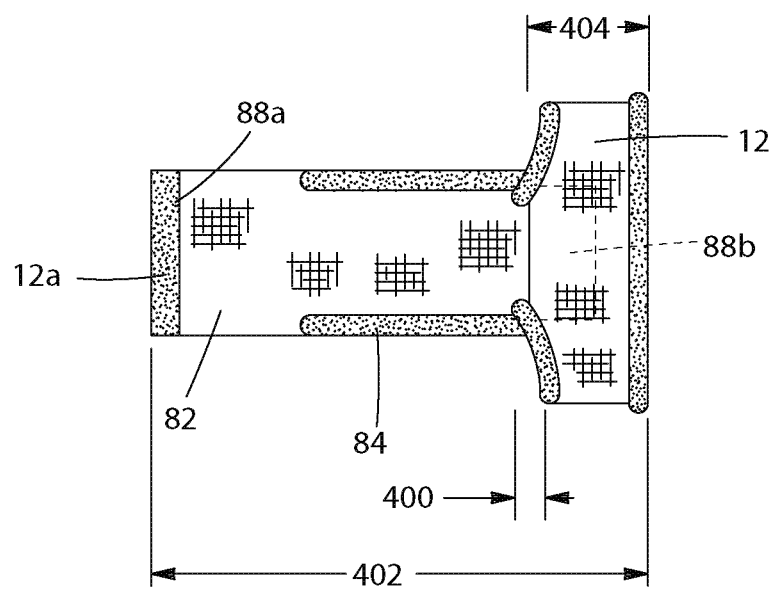
FIG. 17C is a schematic view of first and second waist belts aligned with a chassis in a first configuration.
Figure 17D:
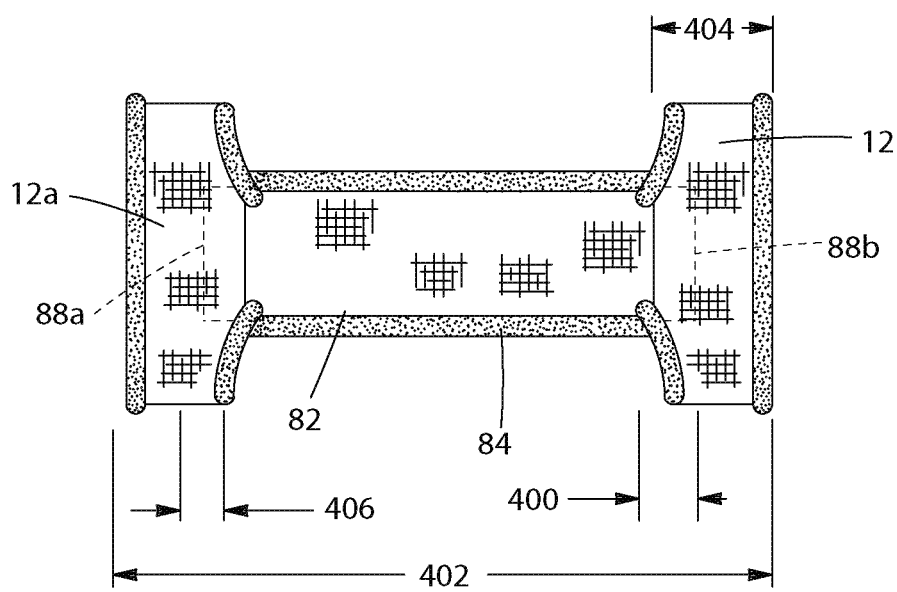
FIG. 17D is a schematic view of first and second waist belts aligned with a chassis in a second configuration.

A similar concept can be applied to a diaper having two waist belts, 12 and 12a. As shown, for example, in FIG. 17C, waist belt 12a may comprise only a band, which may be elastic or inelastic, that is applied at or near front waist region 88a of chassis 82. In particular, waist belt 12a may not comprise ears which extend laterally beyond the edges of chassis 82. The length 404 of waist belt 12, plus the length of chassis 82, plus the length of waist belt 12a, less the extent of overlap 400 between waist belt 12 and chassis 82, equals the length 402 of the diaper. Or, said another way, the extent to which waist belt 12 extends beyond the end edge of chassis 82 determines the length of the diaper 402. In some embodiments, as shown in FIG. 17D, waist belt 12a may be more elaborate, comprising some or all of the features of waist belt 12, as described above. If both waist belt 12 and waist belt 12a comprise ears, the ears of waist belt 12 and the ears of waistbelt 12a may be joined to one another, rather than joining the ears of waist belt 12 to the front waist region 88a of chassis 82.

The waist belt 12 (or, for the remainder of this disclosure, waist belts 12 and 12a) and chassis 82 may be aligned using a spacing device, such as a servo-driven spacing device or a combined cut-and-slip machine. Suitable spacing devices may include those described herein, and, for example, in U.S. Pat. No. 6,450,321 to Blumenthal, et al. Either the waist belt 12 or chassis 82, or both, may be positioned using a spacing device. For example, waist belt 12 may be positioned to overlap chassis 82 using a spacing device while chassis 82 is still an integral part of a continuous web of material (that is, waist belt 12 may be positioned to overlap diaper chassis web 80 before diaper chassis web 80 is cut into discrete chassis 82). Alternatively, chassis 82 may be a separate, discrete part that is itself spaced from other chassis 82 and relative to waist belt 12. As previously described, waist belt 12 may be attached proximate a first longitudinal end of chassis 82. The first longitudinal end may correspond to front waist region 88a or back waist region 88b. Waist belt 12 may further be attached to a second longitudinal end of chassis 82 to form a circumferentially continuous waist opening. The second longitudinal end may correspond to whichever waist region, 88a or 88b, was not identified as the first longitudinal end.

In some embodiments, waist belt 12 or waist belt 12a or both waist belt 12 and waist belt 12a may not extend longitudinally beyond the chassis. As such, that the total diaper length may be equal to the length of the chassis, where the waist belt(s) does not extend beyond the chassis. Similarly, if two waist belts are used, and one waist belt does not extend beyond the chassis, the total diaper length may be equal to the length of the chassis plus the extent of the other waist belt that does extend beyond the chassis. The total diaper length is described herein based on the length of the chassis plus the length of the waist belt(s) extending beyond the chassis. However, it should be understood that the final, finished product may have a length which varies from that dimension somewhat. For example, the diaper or portions of the diaper may be activated, stretched, or otherwise elongated, intentionally or unintentionally, such that the final product is somewhat longer than the length of the chassis plus the length of the waist belt(s) extending beyond the chassis. Or, for example, the diaper may be subjected to a final knife cutting operation after the chassis and the waist belt(s) are aligned, such that the final product is somewhat shorter than the length of the chassis. Similarly, intentional or unintentional exposures to varying temperature, humidity, pressures, and the like may cause variations between the length of the chassis, the length of the waist belt(s) extending beyond the chassis, and the final product length. Put more simply, for a variety of reasons, the length of a diaper when it is used by a caregiver or wearer may differ somewhat from the "total diaper length" at the time during manufacturing when the chassis is joined to the waist belt(s). The total diaper length may be adjusted to account for expected changes in length. The total diaper length may be adjusted by changing the fixed length of chassis 82, the fixed length of waist belt 12 or waist belt 12a, or by changing the extent to which waist belt(s) 12 (and/or 12a) extend longitudinally beyond chassis 82. It should be understood that the "total diaper length" is a nominal measurement, and references to "different" diaper lengths or sizes is not meant to include normal variation in the length of diapers manufactured to the same nominal length specification.

As described in greater detail below, chassis 82 may be folded about a lateral axis. Chassis 82 may be folded prior to attaching waist belt 12 to chassis 82 at one or both longitudinal ends, or if two waist belts 12 and 12a are used, chassis 82 may be folded prior to attaching the ears of waist belt 12 to the ears of waist belt 12a.

With reference to FIGS. 13-16, a description of various types of articles that may be produced in accordance with the methods and apparatuses disclosed herein is provided below to provide a context for subsequent descriptions relating to the operation and structural features embodiments of the processing wheel and processing stations and associated manufacturing processes. Although the following description refers to disposable absorbent articles, in which a diaper chassis and one or more side panels are combined to form an absorbent article, it is to be appreciated that various types of articles may be produced in accordance with the methods and apparatuses described herein. As such, absorbent articles referred to herein may include a single layer or multiple layers of woven or nonwoven material and may include a thermoplastic film.

Figure 13:
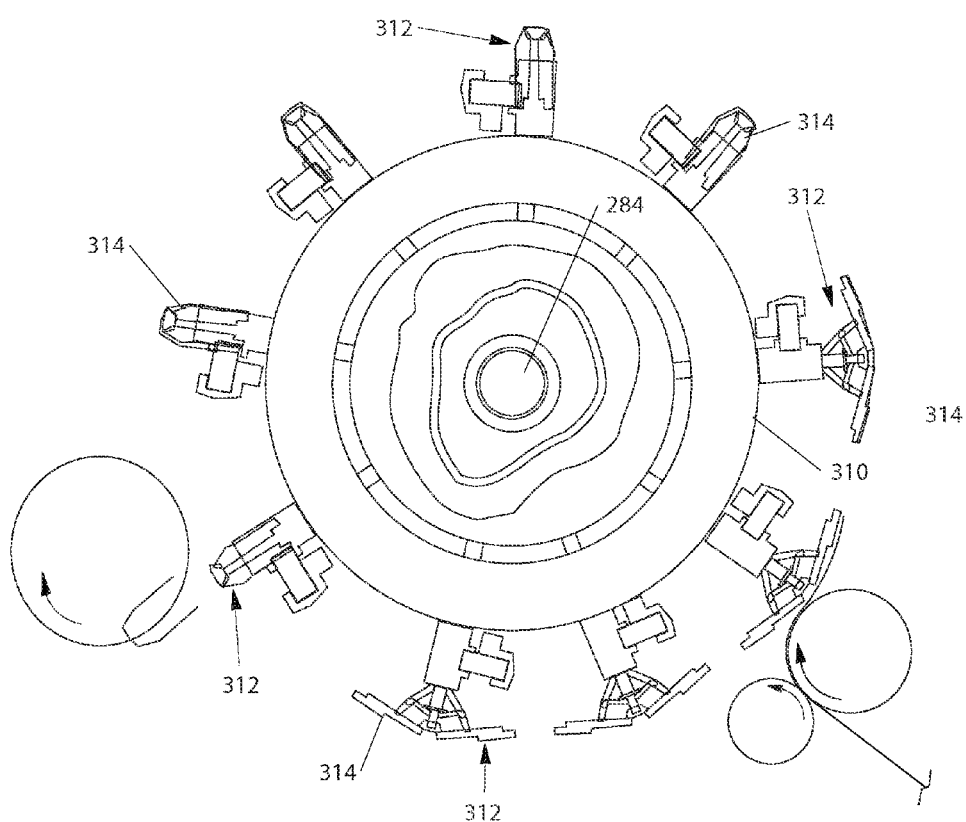
FIG. 13 is a side view of a one embodiment of a machine that folds the diaper chassis and secures free ends of the waist belt to the diaper chassis to form a completed pant-style diaper.

FIGS. 13-16 illustrate one embodiment of a final folding and seaming device 130 that may be used to finish seaming the waist belt to the diaper chassis of FIGS. 2-5 or FIGS. 7-11. The machine 130 generally includes a wheel or hub 310 and a plurality of processing stations 312. As the wheel 310 rotates, the processing stations 312 operate to perform various functions, such as folding the diaper chassis 32 about one or more axes, folding the free ends of the waist belt 12 relative to the diaper chassis 32, and seaming the free ends of the waist belt 12 to the front waist region 38a of the diaper chassis 32. As illustrated in FIG. 13, as the wheel 310 rotates, the individual processing stations 312 move from the receiving location where articulating arms 314 are extended (bottom right of FIG. 13) to a folding location wherein the articulating arms 314 are refracted (top left of FIG. 13). As discussed in more detail below, as the processing stations 312 move through the folding location, the processing stations 312 actuate and fold the combined waist belt 12 and diaper chassis 32 along one or more lateral axes. Actuation of the articulating arms 314 between the extended and retracted positions may be affected by a cam mechanism (not shown). The processing stations 312 may fold the diaper chassis 32 in more than one direction, such as along one or more transverse axes to form a U-shape of the diaper chassis 32 and along gripping members 316 (FIG. 14) to position free ends of the waist belt 12 for engagement with the front waist region 38a of the diaper chassis 32.

As the wheel 310 continues to rotate, the processing stations 312 move from the folding location to a sealing location. As the processing stations 312 move through the sealing location, the processing stations 312 engage the free ends of the waist belt 12 and the front waist region 38a of the diaper chassis 32 to form side seams. The wheel 310 continues to rotate and the processing stations 312 move from the sealing location to a discharge location, where the folded diapers are removed from the wheel 310. The side seams may be formed with various types of connection methods, including for example, pressure bonding, ultrasonic bonding, heat sealing, adhesive attachment, and mechanical attachment. As such, in some arrangements, such as when forming absorbent articles with resealable side seams utilizing, for example, adhesives or mechanical attachments, pressure may be applied to the sealing area to form the side seams. In other arrangements, a heat exchanger and a compression tool may be used to form the side seams. In some embodiments, the heat exchanger forces hot air against the folded blanks, and the compression tool presses the side seams. In some embodiments, cool air may also be applied to the folded, seamed diapers to cool the diapers during compression. It is to be appreciated that depending on the particular configuration, heating and cooling times for the side seam material may vary. It should also be appreciated that FIG. 13 is schematic representation of an embodiment, and the positions and durations of some process steps may vary and/or may overlap, such as the receiving, folding, sealing, and discharge locations.

Figure 14:
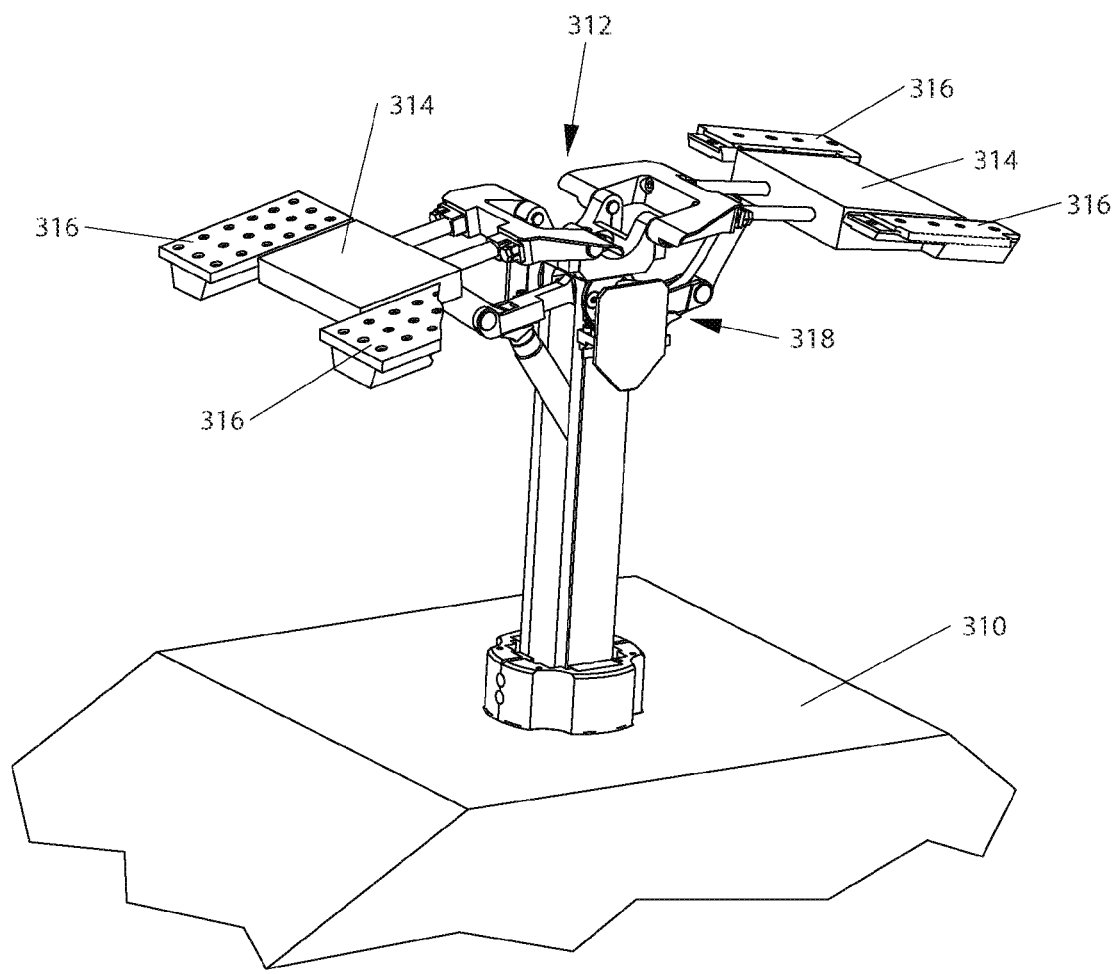
FIG. 14 is a perspective view of one of the articulator arms of the machine of FIG. 13.
Figure 15:
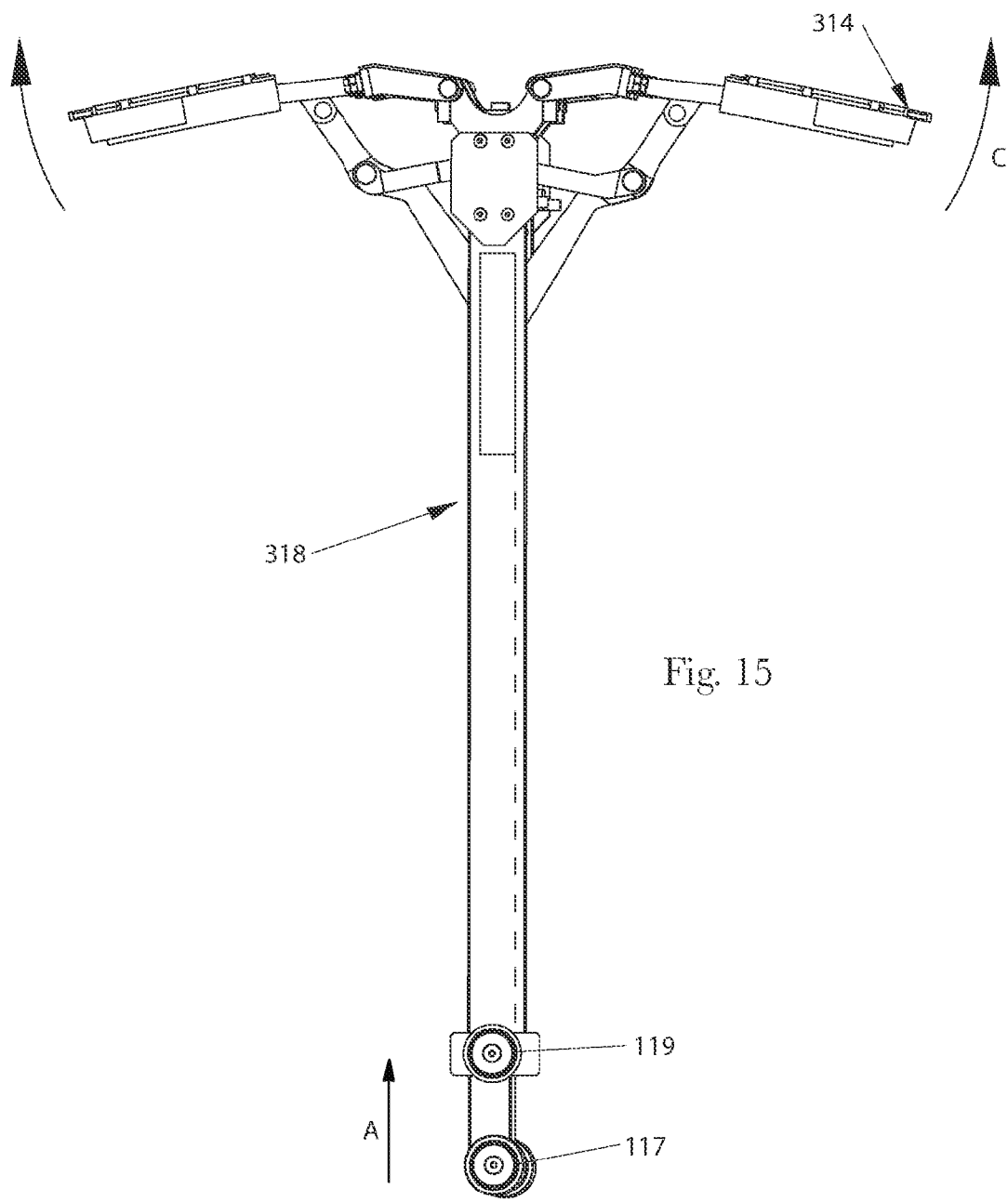
FIG. 15 is a side view of the articulator arm of FIG. 14 in an extended configuration.
Figure 16:
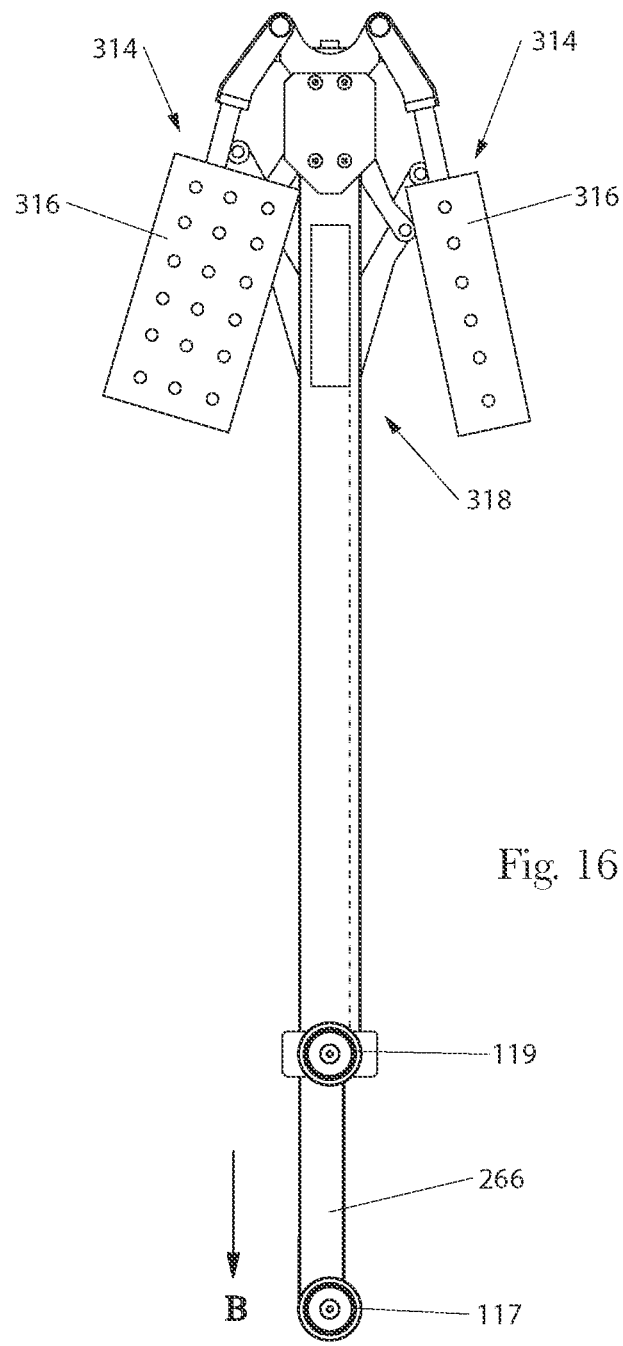
FIG. 16 is a side view of the articulator arm of FIG. 14 in a retracted configuration.

As previously mentioned, the wheel 310 includes a plurality of processing stations 312. For example, the wheel 310 shown in FIG. 13 includes nine processing stations 312. It should be appreciated that the wheel 310 may include more or less processing stations 312 than illustrated herein. For example, some embodiments may include six processing stations 312 and some embodiments may include twelve processing stations 312. As discussed above, the processing stations 312 perform various operations as the wheel 310 rotates. For example, individual diaper chassis 32 disposed on respective processing stations 312 are folded as the wheel 310 rotates. As such, each processing station 312 may include a folding mechanism 318 upon which an individual diaper chassis 32 is disposed as the wheel 310 rotates. One embodiment of a folding mechanism 318 is shown in FIGS. 14-16. In particular, FIG. 14 illustrates a perspective view of the folding mechanism 318 on the wheel 310, FIG. 15 illustrates a side view of the folding mechanism 318 with articulating arms 314 in an extended position; and FIG. 16 illustrates a cross sectional view of the folding mechanism 318 with articulating arms 314 in a retracted position.

As illustrated in FIGS. 14-16, the folding mechanism 318 includes gripper members 316 which hold the diaper chassis 32 and the waist belt 12 while the wheel 310 rotates. In the embodiment of FIGS. 14-16, the gripper members 316 are wider on a trailing edge of the folding mechanism 318 than on a leading edge of the folding mechanism 318. The wider gripper members 316 secure free ends of the waist belt 12, with an advantage being that a contractive waist band can be held under tension. More particularly, with reference to FIGS. 14-16, the individual diaper chassis 32 are transferred from the folding mechanism 318 such that the gripper members 316 are brought into contact with the diaper chassis 32 on one side and the waist belt 12 on the other side. Each gripper member 316 may be configured with a vacuum that exerts a holding force on the diaper chassis 32 or the waist belt 12. The gripper members 316 are configured to rotate and move to fold the diaper chassis 32 and free ends of the waist belt 12. In particular, the diaper chassis 12 and waist belt 12 are delivered to the folding mechanism 318 when the articulating arms 314 are in the extended position (FIG. 15) and the gripper members 316 hold the diaper chassis 32 and waist belt 12 on the folding mechanism 318. As the articulating arms 314 retract (FIG. 15), the diaper chassis 32 is folded about the leg region 36 and the gripper members 316 rotate approximately 90 degrees about the axis of the respective articulating arms 314 during the retraction phase to rotate the free ends of the waist belt 12 relative to the waist regions 38a, 38b of the diaper chassis 32 so that the free ends of the waist belt 12 may be attached or otherwise seamed to the front waist region 38a of the diaper chassis 32. Actuation of the gripper members 316 about the axis of the respective articulating arm 314 may also be affected, or at least triggered, by a cam mechanism (not shown), which may be integral with the aforementioned cam mechanism by which actuation of the articulating arms 314 may be achieved.

Sequentially, the diapers are formed by 1) bifolding the diaper chassis 32, 2) folding the free ends of the waist belt 12 relative to the diaper chassis 32, and 3) seaming the free ends of the waist belt 12 to the front of the diaper chassis 32. In other embodiments, the steps of bifolding the diaper chassis 32 and folding the free ends of the waist belt 12 may be reversed and/or take place nearly simultaneously. Moreover, each of the above steps may be accomplished in separate machines in other embodiments.

The diaper formed by the processes described herein advantageously includes forming the waist belt and diaper chassis from independently laminated webs of material. Thus, control of the diaper is more easily maintained. As a result, diapers formed in accordance with the methods described herein may be manufactured at a high rate of speed. Moreover, the machines described herein may be used to manufacture different sizes of diapers with only minor modifications to the machines themselves. Thus, the machines and methods described herein require a relatively small sized maintenance staff.

Additional advantages flow from the close coupling of the diaper assembly steps. In particular, the diaper assembly steps of 1) separating the diaper chassis, 2) spacing the discrete diaper chassis, 3) attaching the waist belt, 4) bifolding the diaper chassis, 5) folding the free ends of the waist belt; and 6) seaming free ends of the waist belt to the front of the diaper chassis, occur very close together temporally and spatially, thereby boosting manufacturing throughput and improving process control, thereby improving quality of the article (as this process yields a more consistent fold as compared to conventional diaper manufacturing techniques).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling diapers of varying sizes, the method comprising:

providing a series of waist belts, each waist belt having a uniform longitudinal length L1 extending in a machine direction, and wherein each waist belt includes an upper waist region, a lower waist region, and a leg opening region;
providing a series of chassis, each chassis having a uniform longitudinal length L2 extending in the machine direction;
aligning a waist belt from the series of waist belts with a chassis from the series of chassis such that the length of the chassis plus the length of the waist belt extending longitudinally beyond the chassis, if any, equals a total diaper length extending in the machine direction;
varying the alignment of the waist belt and the chassis to change the total diaper length without changing L1 or L2; and
wherein the waist belt and the chassis are aligned using a spacing device.

2. The method of claim 1, wherein the waist belt position is aligned using the spacing device.

3. The method of claim 1, wherein the chassis position is aligned using the spacing device.

4. The method of claim 1, wherein the waist belt is attached to the chassis proximate a first longitudinal end of the chassis.

5. The method of claim 4, further comprising the step of folding the diaper about a lateral axis.

6. The method of claim 1, wherein the chassis comprises two or more strips of elastic.

7. The method of claim 6, wherein the waist belt is attached to at least two of the two or more strips of elastic to form two or more circumferentially continuous leg openings.

8. The method of claim 1, wherein the waist belt is elasticated.

9. The method of claim 8, wherein the waist belt comprises a nonwoven material laminated to an elastic web.

10. The method of claim 8, further comprising ringrolling the waist belt.

11. The method of claim 5, wherein the waist belt is attached proximate to a second longitudinal end of the chassis prior to the step of folding the diaper to form a circumferentially continuous waist opening.

12. A method for assembling diapers of varying sizes, the method comprising the steps of:
providing a web of waist belt material, wherein the web of waist belt material includes at least a first waist belt adjacent to a second waist belt, wherein the first waist belt and the second waist belt each include an upper waist region, a lower waist region, and a leg opening region;
providing a web of diaper chassis material, wherein the web of diaper chassis material includes at least a first chassis adjacent to a second chassis;
separating the first waist belt and the second waist belt;
separating the first chassis and the second chassis;
advancing the first waist belt in a machine direction to a spacing device, the first waist belt having a longitudinal length L1 extending in the machine direction, wherein the spacing device comprises a rotatable drum, wherein the rotatable drum is rotating at a first speed, wherein the first waist belt advances on the rotatable drum;
advancing the first chassis in the machine direction, the first chassis having a longitudinal length L2 extending in the machine direction;
joining the first waist belt with the first chassis to form a first diaper, wherein the longitudinal length L2 of the first chassis plus the length of the first waist belt extending longitudinally beyond the chassis, if any, equals a first diaper length;
advancing a second waist belt in the machine direction to the rotatable drum of the spacing device, the second waist belt having the longitudinal length L1 extending in the machine direction, wherein the rotatable drum of the spacing device is rotating at a second speed, wherein the second speed is different from the first speed;
advancing a second chassis in the machine direction, the second chassis having the longitudinal length L2 extending in the machine direction; and
joining the second waist belt with the second chassis to form a second diaper, wherein the longitudinal length L2 of the second chassis plus the length of the second waist belt extending longitudinally beyond the chassis, if any, equals a second diaper length, wherein the second diaper length is different from the first diaper length.

13. The method of claim 12 further comprising the step of folding the first diaper about a lateral axis.

14. The method of claim 12, wherein the first and second chassis comprise two or more strips of elastic.

15. The method of claim 14, wherein the waist belt is attached to at least two of the two or more strips of elastic to form two or more circumferentially continuous leg openings.

16. A method for assembling diapers of varying sizes, the method comprising the steps of:
providing a web of waist belt material, wherein the web of waist belt material includes a non-woven material bonded to an elastic element, and wherein the web of waist belt material includes at least a first waist belt adjacent to a second waist belt, wherein the first waist belt and the second waist belt each include an upper waist region, a lower waist region, and a leg opening region;
separating a web of waist belt material to form a first discrete waist belt and a second discrete waist belt;
advancing the first discrete waist belt in a machine direction at a first speed, wherein the first discrete waist belt has a longitudinal length L1 extending in the machine direction;
advancing a first chassis in the machine direction, the first chassis having a longitudinal length L2 extending in the machine direction;
joining the first discrete waist belt with the first chassis to form a first diaper, wherein the longitudinal length L2 of the first chassis plus the length of the first discrete waist belt extending longitudinally beyond the chassis, if any, equals a first diaper length;
advancing the second discrete waist belt in the machine direction at a second speed, wherein the second speed is different from the first speed, wherein the second discrete waist belt has the longitudinal length L1 extending in the machine direction;
advancing a second chassis in the machine direction, the second chassis having the longitudinal length L2 extending in the machine direction; and
joining the second discrete waist belt with the second chassis to form a second diaper, wherein the longitudinal length L2 of the second chassis plus the length of the second discrete waist belt extending longitudinally beyond the chassis, if any, equals a second diaper length, wherein the second diaper length is different from the first diaper length.

17. The method of claim 16 further comprising the step of folding the first diaper about a lateral axis.

18. The method of claim 16, wherein the first and second chassis comprise two or more strips of elastic.

19. The method of claim 18, wherein the waist belt is attached to at least two of the two or more strips of elastic to form two or more circumferentially continuous leg openings.

* * * * *